United States Patent
Di Costanzo et al.

[11] Patent Number: 5,958,460
[45] Date of Patent: Sep. 28, 1999

[54] PREPARATION PROCESS FOR A MULTIPARTICULATE PHARMACEUTICAL FORM WITH PLURALITY OF SEQUENCES OF CONTROLLED RELEASE

[75] Inventors: Francis Di Costanzo, deceased, late of Paris, by Jacqueline Di Costanzo, executor; Gérard Cousin, Gallardon; Edouard Gendrot, Vernouillet; Marie-Christine Clee, Treon, all of France

[73] Assignee: Laboratories PROGRAPHARM, Chateauneuf-en-Thymerais, France

[21] Appl. No.: 08/757,060

[22] Filed: Nov. 26, 1996

[51] Int. Cl.[6] .............................. A61K 9/14; A61K 9/54
[52] U.S. Cl. .................. 424/490; 424/458; 424/459; 427/2.15; 427/2.16; 428/403
[58] Field of Search ...................... 424/489, 490, 424/458, 459, 493, 494, 497; 427/2.15, 2.16; 428/403

[56] References Cited

U.S. PATENT DOCUMENTS 4,870,196  9/1989  Thorengaard ........................... 549/410
4,960,596  10/1990  Debregeas et al. ..................... 424/458

*Primary Examiner*—Thurman K. Page
*Assistant Examiner*—James M. Spear
*Attorney, Agent, or Firm*—Caesar, Rivise Bernstein, Cohen & Pokotilow, Ltd.

[57] ABSTRACT

Preparation process for a multiparticulate pharmaceutical form with a plurality of sequences of controlled release of the type which allows the body of the patient to be provided with a sufficient concentration of one or more active ingredients by one or two administration over 24 hours.

4 Claims, 2 Drawing Sheets

PREPARATION PROCESS FOR A MULTIPARTICULATE PHARMACEUTICAL FORM WITH PLURALITY OF SEQUENCES OF CONTROLLED RELEASE

The subject of the invention is a preparation process for a multiparticulate pharmaceutical form with plurality of sequences of controlled release of the type of those which allow, using only one or two administrations, the body of the patient to be provided with, over 24 hours, a sufficient concentration of one or more active ingredients.

Pharmaceutical forms of the type in question lead to the obtaining of a non-linear release in vitro of the active ingredient which is translated in vivo into the presence of one or more absorption peaks of the active ingredient.

In these pharmaceutical forms, the active substance is comprised by a plurality of medicinal particles or spheroids optionally based on neutral centres. Said medicinal particles or spheroids belong to at least two fractions or groups respectively, each fraction being distinguished by its coating the physico-chemical characteristics of which induce a given dissolution profile in vitro of the active ingredient; it is possible that one of the fractions has no coating; the granulometry of these medicinal spheroids is generally from 0.1 to 1.5 mm.

The medicinal spheroids belonging to the different fractions form a group filling for example gelatin capsules or tablets; they are distributed homogeneously within this group.

Pharmaceutical forms of the type in question have existed for about twenty years; the proprietary drug marketed under the trademark SEGLOR is known in particular which is based on dihydroergotamine and which has been on the French market since 1978. They can be prepared by means of processes comprising the use of a set of equipments intended respectively for the preparation of each of the fractions and for the mixing of these fractions once they are prepared.

These known processes involve, due to their complexity, an increase in the cost price of the pharmaceutical forms in question because of the number of operations and pieces of equipment used.

The permanent preoccupation of the pharmaceutical industry being to optimise the cost price of medicaments, the Applicant Company set itself the aim of perfecting a simplified process suitable for producing pharmaceutical forms of the type in question the intrinsic qualities of which are at least equivalent to those of the pharmaceutical forms which already exist while being obtained at a significantly lower unit cost.

And it is to its credit that, after in-depth research, it has perfected a process corresponding to this aim.

The preparation process for a multiparticulate pharmaceutical form with a plurality of sequences of controlled release of the type which allows the body of the patient to be provided with a sufficient concentration of one or more active ingredients by one or two administration over 24 hours, and which comprises at least two fractions of particles distinguished from one another by their respective coatings, is characterized by the fact that the said at least two fractions of particles each one of which corresponds respectively to one of two sequences of controlled release are prepared in a manufacturing step carried out inside a single piece of coating equipment starting from a plurality of similar and homogeneous medicinal uncoated spheroids and from one or more coating materials, the plurality of medicinal uncoated spheroids being divided into as many fractions as there are sequences of controlled release required, all of the said medicinal uncoated spheroid fractions being successively introduced into the single piece of equipment and submitted to a coating treatment which may not be applied to the last fraction, using an equal number of fractions of one or the other of the afore-mentioned coating materials, the coating of a given fraction of medicinal spheroids being carried out in the presence of the medicinal spheroids of the preceding fraction or fractions which have already been subjected to a coating treatment, the plurality of medicinal spheroids thus treated constituting a whole within which there is a homogeneous distribution of the medicinal spheroids of each fraction, the spheroids of each fraction, with the possible exception of those of the last one, having a coating which is characteristic, said plurality of particles then being shaped so as to constitute the sought pharmaceutical form.

In order to prepare the medicinal spheroids, an active substance can be added to neutral centres; to this end, one or other of the following known processes can be used:

application of the active substance to the neutral centre using a turbine application of the active substance to the neutral centre using a fluidized bed.

It is also possible to prepare the medicinal spheroids without using neutral centres, either by direct rotogranulation of the active substance using a fluidized air bed, or by an extrusion-spheronization process.

The single piece of equipment for coating the medicinal spheroids used in the process according to the invention operates continuously or discontinuously according to the principle of the fluidized bed or according to the principle of the standard turbine.

In the case of equipment operating according to the principle of the fluidized bed, this can be constituted by a device of the type of those known in the trade by the name "fluid bed coater", for example that marketed by the Glatt Company under the name GPCG, that marketed by the Hüttlin Company under the name "Kugel-Coater" or that marketed by the Freund Company under the name "Flow coater".

In the case of equipment operating according to the principle of the standard turbine, the turbines marketed by the Mastra Company can be used.

The invention will be able to be even better understood using the additional description which follows and the non-limitative examples which relate to advantageous implementations.

It is to be remembered that the general principle of the release of active ingredients from a coated or uncoated medicinal spheroid corresponds to two main groups of phenomenon:

erosion of the coating polymer with subsequent release of the active ingredient, diffusion of the active ingredient through a coating membrane and/or a cross-linked matrix.

The mixtures of medicinal spheroids comprising at least two fractions of these spheroids at least one of which has a rapid release and at least one other of which has a slow release, are used in the standard fashion in order to allow simultaneous administration via one and the same pharmaceutical form of a so-called "initial dose" of active ingredient (rapid fraction) and of a so-called "maintenance dose" of active ingredient (slow fraction).

Pharmaceutical forms of this type allow therapeutic protocols to be carried out such that, in the body of the patient, a minimal therapeutic concentration of one or more active ingredients is permanently maintained while using only two, or even one administration(s) per day.

Contemplating the preparation of such a pharmaceutical form in accordance with the invention, it is done as follows or in an equivalent way.

First of all uncoated medicinal spheroids are prepared.

In order to do this, the operation can be proceeded with, as indicated in the U.S. Pat. 5,229,135 in the name of the Applicant Company, by fixing a given active ingredient, which is generally in the form of a powder with a granulometry of less than 100 $\mu$m, on preferably spherical neutral centres with a granulometry generally from about 0.1 to about 1.5 mm and, preferably, of 0.4 to 0.7 mm and advantageously constituted by saccharose and starch.

Such neutral centres are commercially available under the name "non-pareils" and are manufactured and marketed inter alia by the Mendell Company.

The neutral centres can also advantageously be constituted by crystals of the active ingredient itself or by excipients for pharmaceutical use such as saccharose, lactose or also cellulose; the granulometry of these neutral centres is generally from about 0.05 to about 0.30 mm and, preferably, 0.15 to 0.20 mm.

In order to fix the active ingredient onto the neutral centres, first of all a film of a binding solution then a layer of pulverulent active substance can be deposited on them, the neutral centres thus treated being subjected to a subsequent drying stage; it is also possible to fix the active ingredient by application of a suspension of this active ingredient in the binding solution. The composition of this suspension falls within the general knowledge of a man skilled in the art.

This sequence of operations is repeated as many times as necessary in order to fix the desired quantity of active substance onto each neutral centre.

In order to complete the preparation, the medicinal spheroids obtained are covered with a polymer film and they are dusted with an agent preventing the formation of clots or anti-clumping agent, for example talc.

In this way a homogeneous fraction of medicinal spheroids is made available containing a given active ingredient.

It is to this homogeneous fraction of medicinal spheroids that the process according to the invention is applied.

With this aim, the aforementioned homogeneous fraction of medicinal spheroids, which constitutes one batch, is divided into at least two fractions the respective sizes of which are determined as a function of the dissolution profile in vitro which is desired to be obtained.

Preferably, two fractions are envisaged.

Furthermore one or more coating compositions are chosen which are generally based on one or more acrylic and/or methacrylic resins in solution in solvents from the group comprising preferably ethanol, acetone, isopropanol and water, pure or mixed; these compositions can include plasticizers, lubricating agents and free-flow agents.

Coating is carried out, in accordance with the invention, using a single and unique piece of equipment comprising, on the one hand, means suitable for putting the medicinal spheroids either in the form of a fluidized bed, or in rotation such as in a standard turbine and, on the other hand, means for spraying the coating compositions.

The equipment in question can be constituted by the device known by the trade term "fluid bed coater"(device for coating using a fluidized bed), for example that marketed by the GLATT Company under the name GPCG.

Firstly, one of the aforementioned fractions of medicinal spheroids is introduced into this single piece of equipment; the aforementioned spheroids are put in the form of a fluidized bed and a first quantity of a first coating composition is applied by spraying to the spheroids in the form of a fluidized bed.

Secondly, the medicinal spheroids of a second fraction of the aforementioned batch are introduced into the equipment, inside which the medicinal spheroids of the first fraction which have just been provided with a coating are maintained in the form of a fluidized bed.

The spheroids of the second fraction are put in the form of a fluidized bed in the presence of the already-coated spheroids of the first fraction, the resulting fluidized bed being composed of coated spheroids and of as yet uncoated spheroids.

Then a second quantity of the aforementioned first coating composition or a first quantity of a second coating composition is applied to the fluidized bed thus constituted.

This new quantity of coating composition is again applied by spraying to the fluidized bed of already-coated spheroids and uncoated spheroids.

In this way a batch of medicinal spheroids is obtained containing a first fraction of spheroids coated with the two successive coatings applied during the first and second coating operations and a second fraction of spheroids coated with a single coating applied during the second coating operation.

In the event that, at the start, the whole of the uncoated medicinal spheroids has been divided into three fractions, the third fraction is then introduced into the equipment within which the aforementioned first and second fractions are maintained in the form of a fluidized bed, which are distinguished from each other by their successive coatings.

The spheroids of this third fraction which are not yet coated are then put in the form of a fluidized bed in the presence of the already-coated spheroids of the aforementioned first and second fractions.

The whole thus constituted can either be used as it is to fill for example gelatin capsules or tablets, or be subjected to a third coating operation using a third fraction of the first coating composition or a second fraction of the second coating composition, or also a first fraction of a third coating composition.

Whatever the solution adopted, one then has at one's disposal a homogeneous whole of medicinal spheroids composed of fractions differing from each other by their successive coatings and therefore endowed with speeds specific to each of them for the release in vitro of the active ingredient, producing the sought homogeneous dissolution profile.

Figure 1:
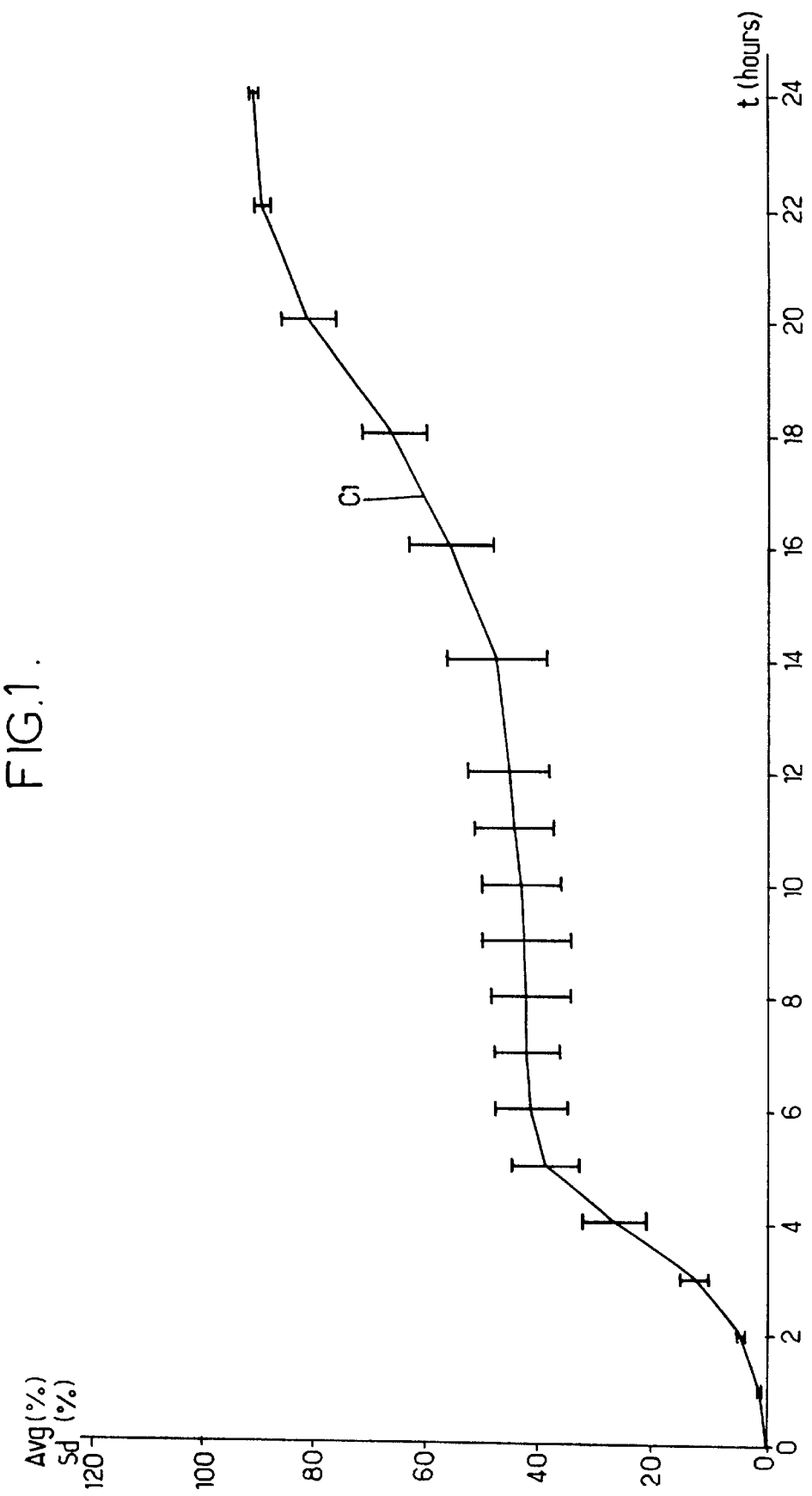
FIGS. 1 and 2 are representations of the results obtained in Examples 1, 2 and Tables 1, 2, wherein the curves represent the variation of active ingredient released as a function of time.

The kinetics for the release of the active substance of the whole thus formed depends on the respective size of the different fractions into which the initial batch of uncoated medicinal spheroids has been divided and the nature and quantities of coating composition used for each operation insofar as these quantities originate from one and the same coating composition or the nature of each coating composition and the quantity used of each composition insofar as several coating compositions which are different from each other are used.

The determination of these parameters, with a view to obtaining a given kinetics for the release in vitro of the active substance, falls within the general knowledge of a man skilled in the art.

The total mass of resin used in the formation of the coating composition, in other words the total mass of polymer mixture required to be applied to the whole batch of medicinal spheroids, is defined as a function of the desired kinetics for the release of the active ingredient; the mass of polymer mixture provided by each fraction of coating composition is defined in such a way that the sum of the masses provided by the different fractions is equal to the total mass as discussed above.

The examples which follow illustrate the determination of the parameters in question.

The operation of the single piece of equipment can be continuous, the successive batches of uncoated medicinal spheroids alternating with the coating operations being introduced successively, for example under reduced pressure.

It can also be discontinuous, the introduction of the uncoated spheroids and of the coating compositions being carried out in batches.

EXAMPLE 1

Preparation of Coated Medicinal Spheroids, Constituting the Pharmaceutical Form According to the Invention and the Active Ingredient of which is Constituted by Diltiazem Hydrochloride or (2S-cis)-3-(acetyloxy)-5-[2-(dimethylamine) ethyl]-2,3-dihydro-2-(4-methoxyphenyl)-1,5-benzothiazepine-4-(5H)-one.

In a first stage, the cores containing the active ingredient, that is the medicinal spheroids, are prepared.

The active ingredient is fixed on spherical neutral supports or centres consisting of saccharose and starch; their average diameter is comprised between 0.4 and 0.7 mm.

A conventional turbine is used and a binding solution containing, in ethanol, 20% by dry weight of a mixture of polymers containing, on the one hand, an acrylic resin, for example that known under the trademark EUDRAGIT RS and, on the other hand, polyvidone, the two polymers being in respective proportions by weight of 75/25.

In order to fix the active substance on the neutral centres, a measured volume of the aforementioned binding solution is sprayed over said centres, then a defined quantity of active ingredient is provided by dusting.

The cycle comprising spraying of the binding solution and dusting of the active ingredient as well as a drying stage, is repeated as many times as necessary to fix the previously-defined total amount of active ingredient on the spherical neutral centres.

The medicinal spheroids thus prepared are dried at ambient temperature in the same turbine for about 12 hours.

A polymer film is then applied to the dried spheroids, previously obtained, by spraying an alcoholic solution of the aforementioned acrylic resin which can be constituted by that known under the mark EUDRAGIT RS (15 to 20% by dry weight); then a defined quantity of talc is applied by dusting and drying is carried out.

This "spraying-dusting-drying" cycle is repeated 12 times in the same turbine.

The spheroids thus obtained, which form a batch with a homogeneity acceptable from the point of view of the content of active ingredient, are used in the process according to the invention.

It is therefore in a second stage that said process is used with a view to coating the medicinal spheroids containing the active ingredient.

The homogeneous batch of medicinal spheroids containing the active ingredient, that is to say Diltiazem HCl, is divided into two fractions the respective sizes of which are determined beforehand as a function of the sought final dissolution profile in vitro.

In the case of the example, the two fractions represent 60 and 40% of the batch respectively.

The first fraction which contains 60% of the mass of medicinal spheroids is introduced into the tank of a piece of equipment for fluidized bed coating, fitted with a Wüster column.

Preferably, the absolute value of the mass of this first fraction of the aforementioned batch does not represent more than 40% of the treatment capacity of the equipment; furthermore it must be sufficient to allow the formation of a fluidized bed.

A first portion, that is to say 44% by mass of the total quantity of a coating composition constituted by a mixture of polymers and plasticizers, free-flow agents and lubricating agents is applied by spraying to this first fraction of active cores put in the form of a fluidized bed.

This first portion of the coating composition is applied in the form of a suspension of 15% of dry matter in a mixture of "ethanol/acetone (60/40; m/m)" solvents; the mixture of polymers is constituted by acrylic resins, namely those known under the marks EUDRAGIT RS and EUDRAGIT RL, in proportions by weight of 95/5; the plasticizers, free-flow agents and lubricating agents are constituted by ethyl phthalate, colloidal silica of the mark AEROSIL R 972 and talc respectively.

All of this suspension is sprayed over the spheroids of the first fraction.

The second fraction of medicinal spheroids (40% of the batch) is then introduced into the tank of the equipment which already contains, in the form of a fluidized bed, the coated medicinal spheroids of the first fraction.

The resulting fluidized bed is therefore composed of medicinal spheroids already provided with a coating (60% of the total) and of spheroids which have not yet been coated (40% of the total), the coated spheroids and those which have not yet been coated being distributed in a homogeneous manner in the fluidized bed.

The second portion, that is to say the remaining 56% by weight of the aforementioned composition based on polymers which must be applied to the whole batch of spheroids, is applied by spraying to this fluidized bed thus formed.

This second portion of the coating composition is applied in the form of a second suspension of 15% of dry matter in a mixture of "ethanol/acetone (60/40; m/m)" solvents; this time, the mixture of polymers contains the two aforementioned acrylic resins EUDRAGIT RS and EUDRAGIT RL in proportions of 90/10.

After spraying of all of this second portion of the coating composition, the batch of medicinal spheroids is dried in the equipment for about 30 minutes at a temperature of 40° C.

Once drying is complete, some of the spheroids are removed from the batch and their dissolution curve is determined.

In order to do this, a paddle dissolution apparatus is used corresponding to that designated under the name Apparatus I of US Pharmacopoeia No. XXIII; purified water is used as the dissolution medium; the conditions for use of the apparatus are 900 ml of purified water and 50 revolutions/minute.

The following are determined for four samples every hour from the 1st to the 12th hour and every two hours from the 12th to the 24th hour:

the quantity of active ingredient released (expressed in % by weight) relative to the total quantity of active ingredient contained in a given sample and the standard deviation (Sd) of the measurements.

The averages (Avg) of the results obtained for the four samples and the corresponding Sd values are grouped together in Table I hereafter and shown by curve $C_1$ in FIG. 1. This curve $C_1$ represents the variation of active ingredient released as a function of time t (expressed in hours).

The result of the examination of this curve $C_1$ shows that the dissolution kinetics of the active ingredient has two successive sequences spreading out over 24 hours.

TABLE I

| t (hours) | 1:00 | 2:00 | 3:00 | 4:00 | 5:00 | 6:00 | 7:00 | 8:00 | 9:00 |
|---|---|---|---|---|---|---|---|---|---|
| Avg (%) | 1.27 | 4.19 | 12.33 | 26.18 | 38.67 | 41.27 | 42.11 | 42.10 | 42.32 |
| Sd (%) | 0.21 | 0.73 | 2.03 | 4.30 | 4.41 | 4.78 | 4.59 | 5.10 | 5.45 |
| t (hours) | 10:00 | 11:00 | 12:00 | 14:00 | 16:00 | 18:00 | 20:00 | 22:00 | 24:00 |
| Avg (%) | 42.73 | 44.03 | 44.36 | 47.19 | 55.38 | 66.03 | 81.29 | 89.48 | 91.13 |
| Sd (%) | 5.03 | 5.11 | 5.20 | 6.56 | 5.53 | 4.15 | 3.55 | 0.97 | 0.91 |

EXAMPLE 2

Preparation of Coated Medicinal Spheroids, Constituting the Pharmaceutical Form According to the Invention and the Active Ingredient of which is Constituted by Verapamil Hydrochloride or α[3-[[2-(3,4-dimethoxyphenyl) ethyl]methylamino]propyl]-3,4-dimethoxy-α-(1-methylethyl)-benzeneacetonitrile.

In a first stage, the cores containing the active ingredient, that is the medicinal spheroids, are prepared.

The active ingredient is fixed on spherical neutral supports or centres constituted by saccharose and starch having an average diameter comprised between 0.4 and 0.7 mm, using the equipment required to be used for the subsequent coating, that is to say a piece of equipment for fluidized bed coating fitted with a Würster column; the active ingredient is introduced to a fluidized bed of neutral centres, created within the equipment, by spraying a binding suspension containing 34% by dry weight of a mixture constituted by Verapamil HCl, polyvidone and polyethyleneglycol 400 in a solvent mixture of isopropanol and ethanol in equal proportions.

When spraying of the suspension is complete, the microgranules are dried in the equipment for 30 minutes at a temperature of 40° C.

In a second stage, the medicinal spheroids thus obtained, which form a batch with a homogeneity acceptable from the point of view of the quantity of active ingredient, are used within the scope of the process according to the invention.

In order to do this, the homogeneous batch of medicinal spheroids containing Verapamil HCl is removed from the equipment and divided into two fractions the respective sizes of which are determined beforehand as a function of the sought final dissolution profile in vitro.

In the case of the example, the two fractions represent 60 and 40% of the batch respectively.

The first fraction which contains 60% of the mass of the medicinal spheroids is reintroduced into the tank of the same fluidized bed coating equipment, fitted with a Würster column.

Preferably, the absolute value of the mass of this first fraction of the aforementioned batch does not represent more than 40% of the treatment capacity of the equipment; furthermore it must be sufficient to allow the formation of a fluidized bed.

A first portion, that is to say 42% by weight of the total quantity of a coating composition consisting of a mixture of polymers and plasticizers, free-flow agents and lubricating agents, is applied by spraying to this first fraction of medicinal spheroids put in the form of a fluidized bed.

This first portion of the coating composition is applied in the form of a suspension of 15% of dry matter in a mixture of "ethanol/acetone (60/40; m/m)" solvents; the mixture of polymers is constituted by acrylic resins, namely those known under the marks EUDRAGIT RS and EUDRAGIT RL, in proportions by weight of 90/10; the plasticizers, free-flow agents and lubricating agents are constituted by ethyl phthalate, silica of the mark AEROSIL R 972 and talc respectively.

All of this suspension is sprayed over the spheroids of the first fraction.

The second fraction of medicinal spheroids (40% of the batch) is then introduced into the tank of the equipment which already contains, in the form of a fluidized bed, the medicinal spheroids coated with the first fraction of the coating composition.

The resulting fluidized bed is therefore composed of medicinal spheroids already provided with a coating (60% of the total) and of spheroids which have not yet been coated (40% of the total), the coated spheroids and those which have not yet been coated being distributed homogeneously in said fluidized bed.

The second portion, that is to say the remaining 58% by weight of the aforementioned composition based on polymers which is required to be applied to the whole of the batch of spheroids, is applied by spraying to this fluidized bed thus formed.

This second portion of the coating composition is applied in the form of a second suspension of 15% of dry matter in a mixture of "ethanol/acetone (60/40; m/m)" solvents; this time, the mixture of polymers again contains the two aforementioned acrylic resins EUDRAGIT RS and EUDRAGIT RL in proportions of 90/10.

After spraying all of this second portion of the coating composition, the batch of medicinal spheroids is dried in the equipment for about 30 minutes at a temperature of 40° C.

Once drying is complete, some of the spheroids are removed from the batch and their dissolution curve is determined.

In order to do this, a paddle dissolution apparatus is used corresponding to that designated by the name Apparatus I of US Pharmacopoeia No. XXIII; purified water is used as the dissolution medium; the conditions for use of the apparatus are 900 ml of purified water and 100 revolutions/minute.

The following are determined for three samples every hour from the 1st to the 12th hour:

the quantity of active ingredient released (expressed in % by weight) relative to the total quantity of active ingredient contained by a given sample and the standard deviation (Sd) of the measurements.

Figure 2:
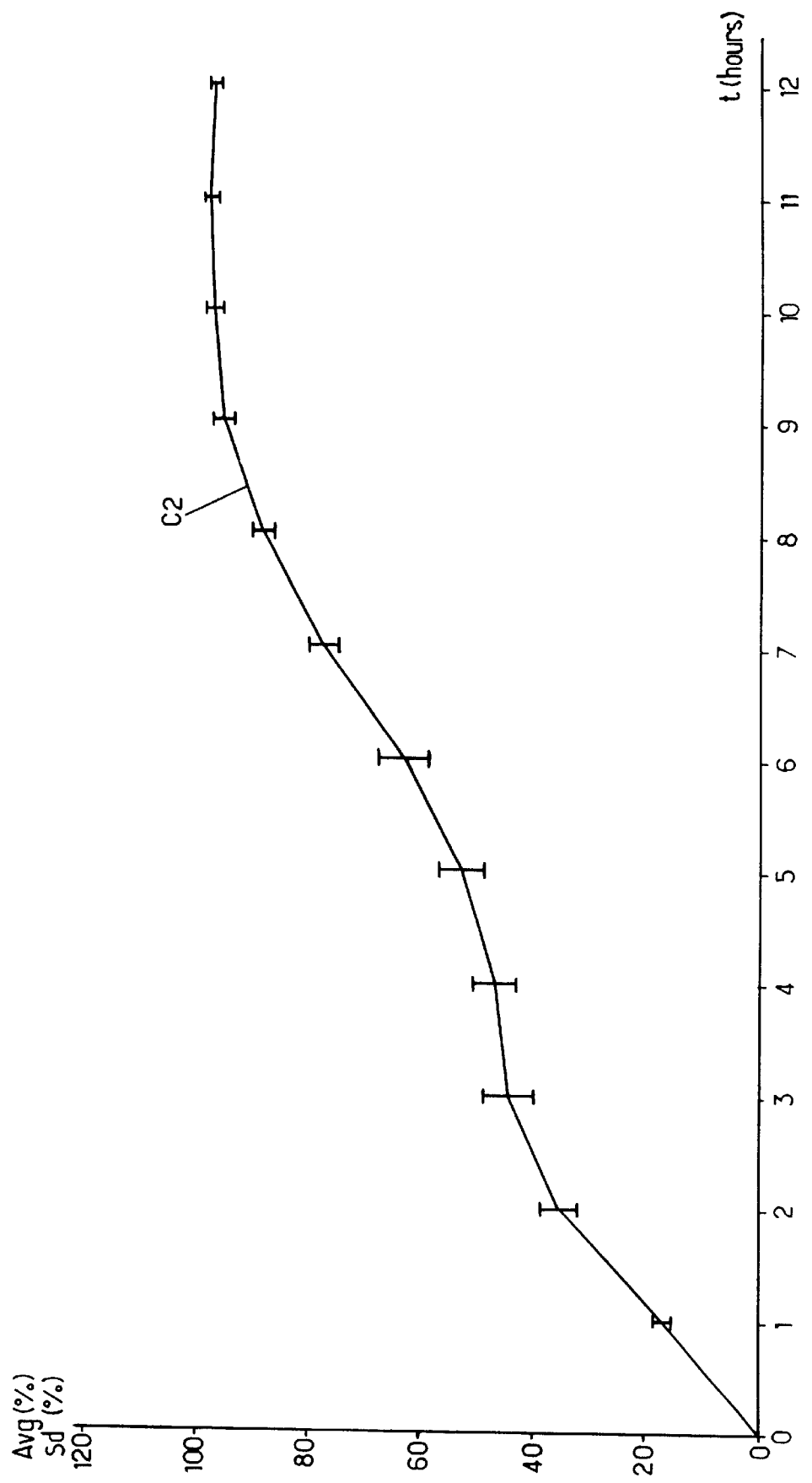

The averages (Avg) of the results obtained for the three samples and the corresponding Sd values are grouped together in Table II hereafter and shown by the curve $C_2$ in FIG. 2. This curve $C_2$ represents the variation of active ingredient released (%) as a function of time t (expressed in hours).

The result of the examination of this curve $C_2$ is that the dissolution kinetics of the active ingredient has two successive sequences spreading out over 12 hours.

TABLE II

| t (hours) | 1:00 | 2:00 | 3:00 | 4:00 | 5:00 | 6:00 |
|---|---|---|---|---|---|---|
| Avg (%) | 16.87 | 35.33 | 43.77 | 46.27 | 51.33 | 62.40 |
| Sd (%) | 1.32 | 3.31 | 4.51 | 3.70 | 4.10 | 4.84 |
| t (hours) | 7:00 | 8:00 | 9:00 | 10:00 | 11:00 | 12:00 |
| Avg (%) | 77.27 | 88.30 | 95.57 | 97.03 | 97.70 | 96.97 |
| Sd (%) | 2.58 | 1.91 | 1.89 | 1.33 | 1.00 | 1.06 |

We claim:

1. Preparation process for a multiparticulate pharmaceutical form with a plurality of sequences of controlled release of the type which allows the body of the patient to be provided with a sufficient concentration of one or more active ingredients by one or two administration over 24 hours, said pharmaceutical form comprising at least of two fractions of particles distinguished from one another by their respective coatings comprising polymer mixture, the coating of each fraction providing the latter with a given kinetics for the release in vitro of the active substance, the said at least two fractions of particles each one of which corresponds respectively to one of two sequences of controlled release being prepared in a manufacturing step carried out inside a single piece of coating equipment starting from a plurality of similar and homogeneous medicinal uncoated spheroids and from one or more coating materials, the plurality of medicinal uncoated spheroids being divided into as many fractions as there are sequences of controlled release required, the said fractions distinguishing from one another only by their respective masses, all of the said medicinal uncoated spheroid fractions being successively and separately from one another introduced into the single piece of equipment and submitted to a coating treatment which may not be applied to the last fractions, using a number of fractions of one or the other of the aforementioned coating materials which is equal at least to the number of fractions of medicinal spheroids minus one, the coating of a given fraction of medicinal spheroids being carried out in the presence of the medicinal spheroids of the preceding fraction or fractions which have already been subjected to a coating treatment and which are not removed from the single piece of equipment once their respective coating steps are terminated, the plurality of medicinal spheroids thus treated which comprise the totality of medicinal spheroids of all the at least two fractions constituting a whole within which there is a homogeneous distribution of the medicinal spheroids pertaining to each fraction, the spheroids of each fraction, with the possible exception of those of the last one, having a coating which is a characteristic of the spheroids of the fraction in question for the release in vitro of the active substance, said plurality of coated medicinal spheroids then being shaped so as to constitute the sought pharmaceutical form.

2. Process according to claim 1, wherein the single piece of equipment for coating the medicinal spheroids operates continuously or discontinuously according to the principle of the fluidized bed and is constituted by a device of the type of those known in the trade under the name "fluid bed coater".

3. Process according to claim 1, wherein the single piece of equipment for coating the medicinal spheroids operates continuously or discontinuously according to the principle of the standard turbine.

4. Preparation process for a multiparticulate pharmaceutical form with a plurality of sequences of controlled release of the type which allows the body of the patient to be provided with a sufficient concentration of one or more active ingredients by one or two administration over 24 hours, said pharmaceutical form comprising at least two fractions of particles distinguished from one another by their respective coatings, the said at least two fractions of particles each one of which corresponds respectively to one of two sequences of controlled release being prepared in a manufacturing step carried out inside a single piece of coating equipment starting from a plurality of similar and homogeneous medicinal uncoated spheroids and from one or more coating materials, the plurality of medicinal uncoated spheroids being divided into as many fractions as there are sequences of controlled release required, all of the said medicinal uncoated spheroid fractions being successively introduced into the single piece of equipment and submitted to a coating treatment which may not be applied to the last fraction, using an equal number of fractions of one or the other of the afore-mentioned coating materials, the coating of a given fraction of medicinal spheroids being carried out in the presence of the medicinal spheroids of the preceding fraction or fractions which have already been subjected to a coating treatment, the plurality of medicinal spheroids thus treated constituting a whole within which there is a homogeneous distribution of the medicinal spheroids of each fraction, the spheroids of each fraction, with the possible exception of those of the last one, having a coating which is characteristic, said plurality of particles then being shaped so as to constitute the sought pharmaceutical form and wherein the manufacture of the medicinal spheroids is achieved starting from neutral centres within the single piece of equipment by application to a fluidized bed of the active substance.

* * * * *